United States Patent [19]

Kauvar

[11] Patent Number: 5,801,225
[45] Date of Patent: *Sep. 1, 1998

[54] SORBENT FAMILIES

[75] Inventor: Lawrence M. Kauvar, San Francisco, Calif.

[73] Assignee: Terrapin Technologies, Inc., San Francisco, Calif.

[*] Notice: The term of this patent shall not extend beyond the expiration date of Pat. No. 5,599,901.

[21] Appl. No.: 690,605

[22] Filed: Jul. 31, 1996

Related U.S. Application Data

[62] Division of Ser. No. 248,538, May 24, 1994, Pat. No. 5,599,901, which is a continuation of Ser. No. 920,335, Jul. 27, 1992, abandoned.

[51] Int. Cl.$^6$ .............................. A61K 38/08; C01K 7/00
[52] U.S. Cl. .............................. 530/344; 530/329
[58] Field of Search .............................. 530/329, 344

[56] References Cited

U.S. PATENT DOCUMENTS 4,694,044 9/1987 Kiniwa .
4,963,263 10/1990 Kauvar .

FOREIGN PATENT DOCUMENTS

WO 86/06487 11/1986 WIPO .
WO 89/09088 10/1989 WIPO .
WO 91/06356 6/1991 WIPO .

OTHER PUBLICATIONS

Marshall, "Three–Dimensional Structure of Peptide–Protein Complexes: Implications for Recognition" *Current Opinion in Structural Biology* 2:904–919 (1992).

Müller, et al., "New Ion Exchangers for the Chromatography of Biopolymers" *Journal of Chromatography* 510:133–140 (1990).

Ohlson, et al., "Novel Approach to Affinity Chromatography Using 'Weak' Monoclonal Antibodies" *Analytical Biochemistry* 169:204–208 (1988).

*Primary Examiner*—Paula K. Hutzell
*Assistant Examiner*—Benet Prickril
*Attorney, Agent, or Firm*—Morrison & Foerster LLP

[57] ABSTRACT

Compounds useful as affinity chromatography supports and as labeled reagents are disclosed. The compounds are peptides which can be constituted in families of positively charged, negatively charged or uncharged small peptides or the amidated forms thereof with varying characteristics as to charge, charge distribution, hydrophobicity, cyclization, and helical conformation propensity.

14 Claims, 5 Drawing Sheets

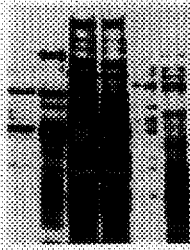
FIG. 5A
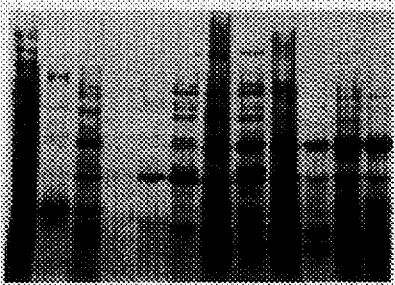
FIG. 5B
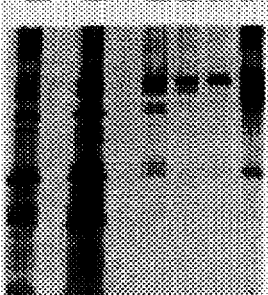
FIG. 5C
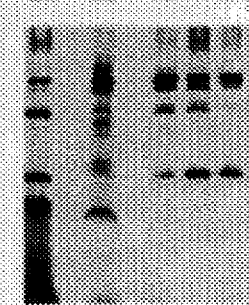

SORBENT FAMILIES

This application is a divisional of application Ser. No. 08/248,538 filed May 24, 1994, now U.S. Pat. No. 5,599,901, which is a continuation of Ser. No. 07/920,335 filed Jul. 27, 1992, now abandoned.

TECHNICAL FIELD

The invention relates to families of affinity ligands useful in separations and purification of biological and other materials. More particularly, the invention concerns families of ligands which provide unique patterns of affinities among candidate moieties which need to be separated.

BACKGROUND ART

Chromatographic separations in the liquid and gas phase are commonplace and exploit a variety of molecular interactions. One general class of chromatographic interactions exploits only a single generalized property, such as interaction with an anion or cation or a hydrophobic stationary phase. Another general category, generally known as affinity chromatography, employs ligands that interact specifically with individual targets, such as antibodies or receptor proteins.

In the chromatographic mode employing ion-exchange supports or hydrophobic supports, the behavior of the molecules is generic with respect to groups—i.e., certain groups of molecules will be readily adsorbed to cation exchangers, others to anion exchangers, others to hydrophobic moieties and the like. These chromatographic techniques generally require large numbers of partitioning events to separate the individual members of these groups. On the other hand, in the "affinity" mode, only a very small class of molecules is adsorbed to the affinity support and all other molecules are unaffected. Thus, this latter method is unable to sort out individual members of large classes of compounds absent a multiplicity of individual steps involving individual affinity ligands.

Additional drawbacks of the foregoing conventional chromatographic methods reside in the difficulty of eluting the adsorbed materials in a biologically active form. Both the eluates from affinity chromatography using immunoglobulins, and those containing materials adsorbed to ion exchangers, show distortions in the molecular conformation of the contained materials (Ohlson, S. et al. *Anal Biochem* (1989) 169:204; Muller, W., *J Chromatog* (1990) 510:133).

The foregoing forms of chromatographic separations can be thought of as "single mode" procedures wherein only a particular property, such as charge, hydrophobicity, or specific affinity for a ligand is made the basis for separation. There has been limited experience with "mixed mode" sorbents where a number of features of the adsorbing moieties are employed. Such approaches are described in U.S. Pat. No. 4,694,044 wherein random copolymers of amino acids are used as a chromatographic matrix. Commercially available materials for the "mixed mode" approach include Polysorb MP3 (Interaction Chemicals), which is a polymeric sorbent containing both C-18 and sulfonic acid moieties. In addition, a series of Cibacron Blue dyes attached to DEAE or CH agarose are commercially available from Bio Rad.

PCT application WO 89/09088 describes, generally, the approach of using paralog sorbents for achieving mixed mode chromatography at a molecular level.

As described in this publication, polymeric materials are constructed from individual monomer units in such a manner as to systematically vary at least two properties across the group of paralogs, thus providing a maximally diverse spectrum of affinities for a variety of target molecules. The present invention is directed to particular families of such paralogs which are designed to mimic, to systematically varying degrees, the properties of commonly used anion or cation exchange resins, such as diethylaminoethyl cellulose (DEAE) and carboxymethyl cellulose (CMC). These sorbents may be used as families to determine ideal supports for separation of particular mixtures, or singly for the actual separation of the members of these mixtures. In addition, these materials are helpful in selective elution of members of the groups of adsorbed molecules.

DISCLOSURE OF THE INVENTION

The invention provides individual sorbents and families of sorbents which mimic the properties either of DEAE or CMC with varying degrees of fidelity. These sorbents are short peptides or close analogs thereof wherein the individual amino acid residues are selected to provide overall positive or negative charge and/or varying patterns of charge distribution, hydrophobicity, molecular rigidity and helical conformation propensity.

Thus, in one aspect, the invention is directed to a family comprised of at least three peptides which peptides display a range of affinities for a protein in comparison to the affinity of DEAE for said protein, and wherein the peptides of said family are composed of small numbers of amino acid residues containing a preponderance of positively charged amino acids and wherein each peptide of the family differs from all other peptides of the family with respect to at least two parameters selected from the group consisting of total positive charge, spatial arrangement of positive charge, cyclization, and helical conformation propensity.

In another aspect, the invention is directed to compounds which mimic CMC. In this aspect, the invention is directed to a family of at least three peptides which peptides display a range of affinity for a protein in comparison to the affinity of CMC for said protein, wherein the peptides of the family are composed of small numbers of amino acid residues containing a preponderance of negatively charged amino acids, and wherein each peptide of the family differs from all other peptides of the family with respect to at least two parameters selected from the group consisting of total negative charge, spatial arrangement of negative charge, cyclization, and helical conformation propensity.

In still another aspect, the invention is directed to peptides that mimic uncharged sorbents.

In additional aspects, the invention is directed to the compounds of the invention coupled to solid supports wherein the solid supports do not provide a significant degree of background ion exchange character and to the use of a compound of the invention coupled to such supports in chromatographic separations.

In other aspects, the invention is directed to methods to elute adsorbed materials using the compounds of the invention as eluting agents.

In still other aspects, the invention is directed to the compounds of the invention per se, individually or in groups.

BRIEF DESCRIPTION OF THE DRAWINGS

1A shows the quantity of BSA in the flow-through (FT) fractions.

FIG. 4 shows the adsorption isotherm for BSA on DEAE and on selected sorbents of the invention, P3 and P4.

FIG. 5 shows photocopies of a series of SDS-PAGE determinations of flow-through fractions and retained eluates from a series of separations using DEAE and the sorbents of the invention and starting with a yeast cell lysate.

MODES OF CARRYING OUT THE INVENTION

Figure 1A:
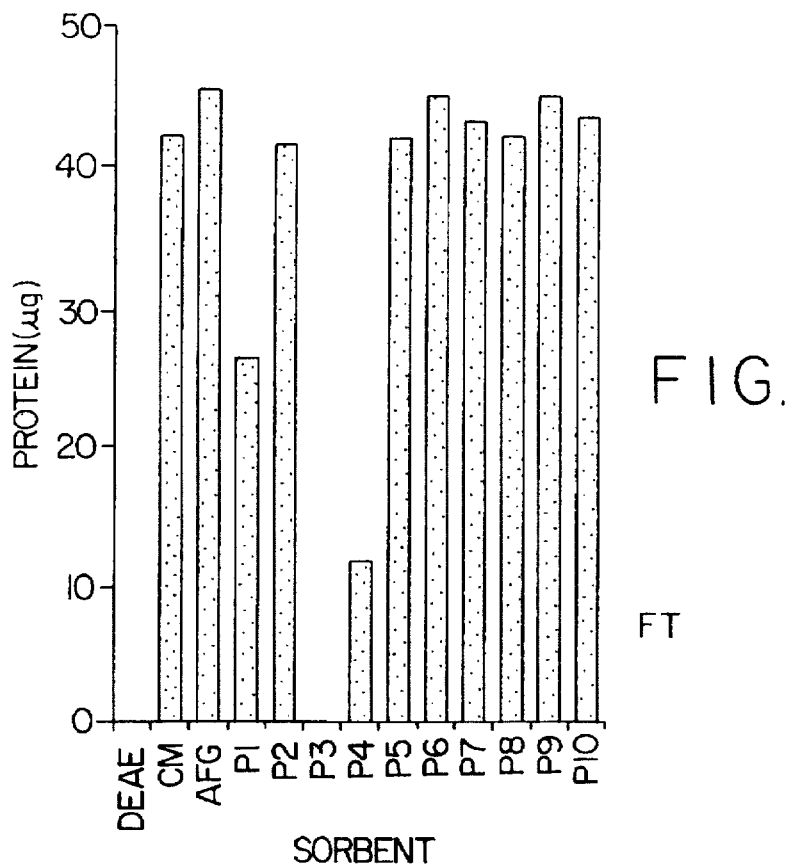
FIG. 1 shows the behavior of bovine serum albumin (BSA) with respect to adsorption to DEAE, CMC, Affi-Gel 10 (AFG) and ten different sorbents of the invention. FIG.
FIG. 1B shows the amount of BSA which has been adsorbed and eluted (RE).

In general, the sorbents of the invention are short peptides wherein a series of amino acids provides a net positive or negative charge to the peptide, depending on the desirability of mimicking cation or anion exchange stationary phases, such as DEAE or CMC, or wherein the peptide has a net charge of zero wherein non-charged sorbents are mimicked. This sequence of amino acids is optionally bracketed by cysteine residues to provide cyclization through disulfide bond formation; alternatively, cyclization is provided by amide or ester formation. In addition, the amino acid sequence of the peptide is optionally preceded by an amino acid that influences helix formation to provide variance in helical conformation propensity.

Preferred negatively charged amino acids are the gene-encoded aspartic or glutamic acid residues; however, other negatively charged amino acid residues not encoded by the gene, such as cysteic acid, may also be used. Preferred positively charged amino acids include ornithine and gene-encoded lysine and arginine residues. Other positively charged amino acid residues included and preferred are homolysine and homoarginine. Of course, all of the residues in the sequence need not bear a charge; there must simply be a preponderance of the appropriately charged residues, where an overall charge is desired.

Preferred neutral amino acids are the low molecular weight forms such as glycine, serine, alanine, and threonine, and their nonencoded analogs such as sarcosine (Sar) and β-alanine (β-ala). If hydrophobic character is desired to be superimposed on the charged structure, valine, leucine, isoleucine, phenylalanine, tryptophan, or methionine are preferred, as well as the nonencoded phenylglycine (Phg), N-methyl isoleucine (N-MeIle), norleucine (Nle), and cyclohexyl alanine (Cha).

Isosteric pseudopeptide linkages, generally known in the art, can also substitute for one or more peptide linkages in the sorbents of the invention. These linkages include $-CH_2NH-$, $-CH_2-S-$, $-CH_2CH_2-$, $-CH=CH-$ (cis and trans), $-COCH_2-$, $-C(OH)CH_2-$ and $-CH_2SO-$.

If cyclic forms of the peptides are desired, the charge-conferring or neutral sequence is bracketed by residues for formation of disulfide or other bridges. Formation of disulfide bridges is generally between cysteine residues bracketing the charge-conferring or neutral sequence; however, homocysteine residues or other sulfhydryl-containing amino acid residues may be substituted for one or both of the cysteine residues. In addition, amide or ester bridges may be employed wherein the amide or ester is formed by reaction of substituents of side chains of the bracketing amino acids, or of the side-chain functional groups of one amino acid internal to the peptide with the carboxyl group at the C-terminus. For example, ester formation between the hydroxyl group of a threonine residue and a carboxyl group of an aspartic acid residue, or between the hydroxyl group of threonine and the C-terminal carboxy results in a bridging ester; reaction between the amino group of the lysyl side chain and the carboxyl group of a glutamic side chain or with the C-terminal carboxyl group results in a bridging amide.

If helix formation is to be encouraged, a helical conformation propensity-controlling residue is included at the N-terminus. Preferred are α-amino isobutyric acid (Aib) if helix formation is to be encouraged or 2-aminobutyric acid (Abu) if it is not.

The peptides of the invention are preferably amidated at the C-terminus.

In one embodiment, a family comprised of at least three peptides that display a range of affinities for a protein in comparison to the affinity of DEAE for the protein is disclosed. The peptides of the family are of small numbers of amino acids containing a preponderance of positively charged amino acids, and the C-terminal extended and the amidated forms thereof. Each peptide of the family differs from all other peptides of the family with respect to at least two parameters selected from the group consisting of total positive charge, spatial arrangement of positive charge, cyclization, and helical conformation propensity.

The peptides are selected from those of the formula:

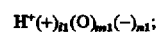

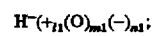

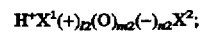

and

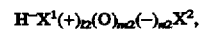

and their 1–2 C-terminal amino acid extended forms and the amides thereof, wherein $H^+$ represents a neutral amino acid which promotes helix formation; $H^-$ represents a neutral amino acid which does not promote helix formation, "+" represents a positively charged amino acid residue; "O" represents a neutral amino acid residue; "−" represents a negatively charged amino acid residue; $X^1$ and $X^2$ represent amino acid residues capable, together, of bridge formation; and l1, m1, n1, l2, m2, and n2 are integers subject to the following restrictions:

l1+m1+n1=4–7;

l1>n1;

l2+m2+n2=3–5;

and l2>n2;

and wherein said peptide optionally contains one or more pseudopeptide linkage.

The nature of the amino acid residues indicated by plus, zero and minus has been set forth hereinabove. $X^1$ and $X^2$ are preferably cysteine residues, or may be other residues capable of forming disulfide-bridges, or residues capable of forming esters or amides. The amidated forms of the peptides of the invention are preferred; it is to be noted that the number of amino acid in the peptides is somewhat arbitrary and, correspondingly, short C-terminal extensions provide compounds that are also included within the scope of the invention.

Further, a family of at least three peptides which peptides display a range of affinity for a protein in comparison to the affinity of CMC for the protein is disclosed. The peptides of the family are of small numbers of amino acids containing a preponderance of negatively charged amino acids. Each peptide of the family differs from all other peptides of the family with respect to at least two parameters selected from the group consisting of total negative charge, spatial arrangement of negative charge, cyclization, and helical conformation propensity.

The peptides are selected from those of the formula:

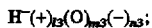

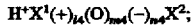

and

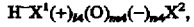

and their 1–2 C-terminal amino acid extended forms and the amides thereof, wherein $H^+$ represents a neutral amino acid which promotes helix formation; $H^-$ represents a neutral amino acid which does not promote helix formation, "+" represents a positively charged amino acid residue; "O" represents a neutral amino acid residue; "–" represents a negatively charged amino acid residue; $X^1$ and $X^2$ represents amino acid residues capable, together, of bridge formation; l3, m3, n3, l4, m4, and n4 are integers subject to the following restrictions:

l3+m3+n3=4–7;

l3<n3;

l4+m4+n4=3–5;

and l4<n4;

and wherein said peptide optionally contains one or more pseudopeptide linkage.

As will be evident, the negatively charged peptides of this group are similar to those set forth above as mimics for DEAE, except for the requirement that negative amino acids predominate.

In yet another aspect, a family of at least three peptides, which peptides display a range of affinity for a protein in comparison to the affinity of a neutral solid support for said protein is disclosed. The peptides of the family are of small numbers of amino acids and have a net neutral charge. Each peptide of the family differs from all other peptides of the family with respect to at least two parameters selected from the is group consisting of hydrophobicity, spatial arrangement of charges, cyclization, and helical conformation propensity. The peptides are selected from those of the formula:

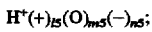

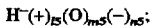

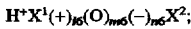

and

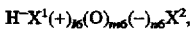

and their 1–2 C-terminal amino acid extended forms and the amides thereof, wherein $H^+$ represents a neutral amino acid which promotes helix formation; $H^-$ represents a neutral amino acid which does not promote helix formation, "+" represents a positively charged amino acid residue; "O" represents a neutral amino acid residue; "–" represents a negatively charged amino acid residue; $X^1$ and $X^2$ represent amino acid residues that form a bridge; l5, m5, n5, l6, m6, and n6 are integers subject to the following restrictions:

l5+m5+n5=4–7;

l5=n5;

l6+m6+n6=3–5;

and l6=n6;

and wherein said peptide optionally contains one or more pseudopeptide linkages.

Again these compounds are similar to those set forth above, except that the net charge on the molecule is neutral. Thus, the descriptive elements with respect to the foregoing compounds apply here, as well.

The peptides of the invention may be supplied individually in uncoupled form, or may be linked to an additional moiety that is other than a simple extension of the peptide. Such additional moiety may be a solid support, a label, a drug or other biologically active material and/or a nonpeptide linker for coupling to the foregoing. When bonded to solid support, the support is other than agarose support with uncapped carboxyl groups. Labels may be, for example, radiolabels, enzyme labels or fluorescent or chromogenic. The solid support or label may be directly bound to the peptide or joined through a linker such as those sold by Pierce Chemical Co., Rockford, Ill.; or may be joined through a spacing polymer such as polyethyleneglycol (PEG) or other bifunctional polymer.

Preparation of the Invention Compounds

The peptides of the invention are synthesized using conventional techniques including, preferably, solid-phase peptide synthesis, although solution-phase synthesis may also be used. In solid-phase synthesis, for example, the synthesis is commenced from the carboxyl-terminal end of the peptide using an alpha-amino protected amino acid. t-Butyloxycarbonyl (Boc) protective groups can be used for all amino groups even though other protective groups are suitable. For example, Boc-Ser-OH, Boc-Asp-OH, Boc-Orn-OH, or Boc-Tyr-OH can be esterified to chloromethylated polystyrene resin supports. The polystyrene resin support is preferably a copolymer of styrene with about 0.5 to 2% polystyrene polymer to be completely insoluble in certain organic solvents. See Stewart et al., *Solid-Phase Peptide Synthesis* (1989) W. H. Freeman Co., San Francisco and Merrifield, *J Am Chem Soc* (1963) 85:2149–2154. These and other methods of peptide synthesis are also exemplified by U.S. Pat. Nos. 3,862,925, 3,842,067, 3,972,859, and 4,105,602.

The synthesis may use manual techniques or may be done automatically, employing, for example, an Applied BioSystems 430A Peptide Synthesizer (Foster city, Calif.) or a Biosearch SAM II automatic peptide synthesizer (Biosearch, Inc., San Rafael, Calif.), following the instructions provided in the instruction manual supplied by the manufacturer.

The intermediates which are constructed in accordance with the present disclosure during the course of synthesizing the present peptide compounds are themselves novel and useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds. Since the peptide sequences are relatively short, recombinant production is facilitated.

Peptide analogs which include alternative-linking moieties are prepared as described by Spatola, A. F., Vega Data (March 1983), Vol. Issue 3, "Peptide Backbone Modifications" (general review; Spatola, A. F., in "Chemistry and Biochemistry of Amino Acids Peptides and Proteins", B. Weinstein, eds., Marcel Dekker, New York, p. 267 (1983) (general review); Morley, J. S., *Trends Pharm Sci* (1980), pp. 463–468 (general review); Hodson, D., et al., *Int J Pept Prot Res* (1979) 14:177–185 (—CH$_2$C—H$_2$—S); Hann, M. M., *J Chem Soc Perkin Trans* I (1982) 307–314 (—CH═CH—, cis and trans); Almquist, R. G., et al., *J Med Chem* (1980) 23:1392–1398 (—COCH$_2$—); Jennings-White, C., et al., *Tetrahedron Lett* (1982) 23.2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—CH(OH) CH$_2$—); and Hruby, V. J., *Life Sci* (1982) 31:189–199 (—CH$_2$—S—).

Uses of the Invention Compounds

The peptides of the invention are particularly useful in procedures for separation and purification of various analytes using chromatographic techniques. In one method of use, the peptides of the invention, which, for example, mimic in various degrees the anion-exchange properties of DEAE, are useful to provide alternative elution patterns for mixtures of components or for separation of individual substances.

For use in these techniques, the peptides of the invention are coupled to solid supports. Coupling can be effected through standard coupling techniques, depending on the nature of the support and-the functional groups available on the peptides. General methods for coupling peptide residues to solid supports are well known in the art.

Useful solid supports include inert supports such as derivatized silica and control pore glass or the various polysaccharide supports such as dextran and agarose. Agarose supports may be used provided they do not contain uncapped carboxyl groups as a result of the coupling. In one typical procedure, the hydroxyl groups contained in the agarose are partially oxidized to carboxyl moieties which are then further derivatized, for example, with N-hydroxysuccinimide. The resulting succinylated support is then reacted with the amidated form of the invention peptides-to obtain the derivatized support. Care must be taken-to derivatize all of the available carboxyls with the peptides of the invention or otherwise to cap free carboxyl groups; otherwise, the presence of the carboxyl anions in the uncapped support will interfere with the affinity attributes of the ligand-coupled column. Accordingly, if agarose is used as a solid support and the oxidized form is utilized for coupling, care must be taken to ensure that no uncapped carboxyl groups are present in the finished product.

However, various alternate solid supports other than agarose may also be used, as set forth above, and wide variety of coupling techniques may be employed, as is commonly understood.

The coupled supports can be used singly or in groups, depending on the nature of the application. For separations of complex mixtures, or for purification of a desired substance from a mixture, individual coupled supports, preferably in the form of columns, can be used using standardized chromatographic procedures. If it is desired to assess the appropriate support for separation of mixtures, groups of the derivatized supports, preferably at least sets of three supports, derivatized to different members of the families of peptides of the invention may be employed. The three or more members should be selected so as to vary in at least one parameter typically selected from the group consisting of the total charge contained in the molecule; the spatial arrangement of the charge, if any; cyclization, and helical conformation propensity (in the case of charged affinity ligands), and selected from the group consisting of hydrophobicity, spatial arrangement of hydrophobicity, cyclization and helical conformation propensity in the case of uncharged ligands.

Such a set of ligands may also be used to provide a profile of an analyte which exhibits binding to the derivatized supports. In this application, sets of supports are used having diversity in the properties mentioned above, as appropriate, and the pattern of affinity used as an identifying fingerprint for the analyte. The characteristics which provide the profile may include crude measures such as percentage of the analyte adsorbed by the various columns, or may include more refined measurements such as elution times and the like. Establishing the identifying characteristics of the profile based on the behavior of the analyte with respect to a set of such derivatized supports is well within ordinary skill.

In addition, for applications which require the coupling of the peptides to solid supports, the compounds of the invention can be used in a converse application—namely, to effect the elution of analytes previously adsorbed to other solid supports. Depending on the affinity of the peptides of the invention for the affinity ligands contained on the adsorbing support, selective elution of particular analytes and corresponding profiling can also be effected.

Preferred Embodiments

In one group of preferred embodiments of the compounds of the present invention, the peptides are the amidated forms of peptides of the formula (SEQ ID NO:1):

(Aib/Abu)-AA$_2$-AA$_3$-AA$_4$-AA$_5$-AA$_6$-AA$_7$, wherein AA2 is cys, orn, lys, asp, glu, ser, gly, ala, phe or tyr;
each of AA$_3$, AA$_4$ AA$_5$ and AA$_6$ is independently orn, lys, asp, glu, ser, gly, ala, phe or tyr,
AA$_7$ is absent or is cys, orn, lys, asp, glu, ser, gly, ala, phe or tyr, and wherein the parameters set forth with regard to the peptides in the various families described above are maintained.

Particularly preferred are the set of peptides P1–P10 set forth in Example 1 hereinbelow, wherein P1–P5 represent members of the family of positively charged peptides; P6, P7 and P9 represent members of the family of negatively charged peptides; and P8 and P10 represent members of the neutral family. Also preferred as additional members of the positively charged amino acid family are (SEQ ID NO:2 through SEQ ID NO:11):

```
      1    2    3    4    5    6
aib—lys—orn—orn—orn—orn—NH2;

1    2    3    4    5    6    7
aib—orn—lys—ser—ser—orn—orn—NH2;

1    2    3    4    5    6    7
Abu—cys—lys—orn—lys—orn—cys—NH2;

1    2    3    4    5    6    7
aib—cys—ser—orn—lys—ser—cys—NH2;

1    2    3    4    5    6    7
aib—orn—ala—orn—orn—orn—ser—NH2;

1    2    3    4    5    6
aib—lys—lys—lys—lys—orn—NH2;

1    2    3    4    5    6    7
Abu—cys—orn—ala—orn—orn—cys—NH2;

1    2    3    4    5    6    7
aib—cys—asp—orn—orn—lys—cys—NH2;

1    2    3    4    5    6    7    8
aib—phe—orn—orn—orn—ser—ser—orn—NH2;

1    2    3    4    5    6
aib—tyr—ala=orn—ala—tyr—NH2.
```

Other preferred members of the negatively charged family (SEQ ID NO:12 through SEQ ID NO:21) include:

```
          1    2    3    4    5    6
P1 = aib—asp—glu—asp—asp—glu—NH2;

1    2    3    4    5    6    7
P2 = aib—asp—glu—ser—ser—asp—asp—NH2;

1    2    3    4    5    6    7
P3 = Abu—cys—glu—gly—glu—gly—cys—NH2;

1    2    3    4    5    6    7
P4 = aib—cys—ser—asp—glu—ser—cys—NH2;

1    2    3    4    5    6    7
P5 = aib—asp—ala—glu—glu—orn—ser—NH2;

1    2    3    4    5    6
P6 = Abu—asp—asp—asp—asp—asp—NH2;

1    2    3    4    5    6    7
P7 = Abu—cys—glu—asp—ser—asp—cys—NH2;

1    2    3    4    5    6    7
P8 = aib—cys—asp—orn—glu—asp—cys—NH2;

1    2    3    4    5    6    7    8
P9 = Abu—phe—asp—glu—asp—ser—ser—orn—NH2;

1    2    3    4    5    6
P10 = aib—tyr—asp=gly—ala—tyr—NH2.
```

Additional preferred members of the family of neutral peptides (SEQ ID NO:22 through SEQ ID NO:31) include:

```
          1    2    3    4    5    6
P1 = aib—gly—ser—ser—gly—ser—NH2;
```

-continued
```
          1    2    3    4    5    6    7
P2 = aib—orn—asp—ser—ser—orn—orn—NH2;

1    2    3    4    5    6    7
P3 = Abu—cys—orn—glu—glu—orn—cys—NH2;

1    2    3    4    5    6    7
P4 = aib—cys—ser—orn—asp—ser—cys—NH2;

1    2    3    4    5    6    7
P5 = aib—asp—ala—glu—ala—orn—ser—NH2;

1    2    3    4    5    6
P6 = aib—lys—asp—lys—asp—ser—NH2;

1    2    3    4    5    6    7
P7 = Abu—cys—lys—asp—orn—asp—cys—NH2;

1    2    3    4    5    6    7
P8 = aib—cys—ala—ala—orn—asp—cys—NH2;

1    2    3    4    5    6    7    8
P9 = Abu—phe—ala—asp—ala—ser—ser—orn—NH2;

1    2    3    4    5    6
P10 = aib—phe—ala=ser—ala—tyr—NH2.
```

The following examples are intended to illustrate, but not to limit, the invention.

EXAMPLE 1

Synthesis of Paralog Sorbents

Paralog sorbents were synthesized as individual paralog peptides and coupled to N-hydroxy-succinimide activated agarose (Affi-Gel 10) (~4 μmole/mL sorbent settled bed volume (SBV) unless otherwise indicated) according to the manufacturer's recommendation. The loading density was calculated by quantitating non-attached paralog by HPLC after coupling; the difference between the initial peptide amount in the coupling mixture and the amount present post-coupling, after washing the beads, was considered to be covalently attached to the agarose sorbent. All peptides were synthesized by Multiple Peptide Systems (La Jolla, Calif.), Advanced Chemtech (Louisville, Ky.), or Coast Scientific Products (La Jolla, Calif.).

A slurry of each sorbent was placed in replicate wells of a membrane-bottomed (flow-through) 96-well test plate (Silent Monitor™, Pall Biosupport Corporation, Glen Cove, N.Y.) effectively creating miniature "columns" of 150 μL SBV. The wells of such Sorbent Plates were filled with storage buffer and the plates sealed and refrigerated until further use. For long term storage of the Sorbent Plates, 2% glycerol and 0.01% Na-azide in TE (see Example 2) was used. All reagents and steps were at room temperature.

The paralogs (P1–P10) synthesized were as follows (SEQ ID NO:32 through SEQ ID NO:41):

```
          1    2    3    4    5    6
P1 = aib—orn—orn—orn—orn—orn;

1    2    3    4    5    6    7
P2 = aib—orn—orn—ser—ser—orn—orn;

1    2    3    4    5    6    7
P3 = Abu—cys—orn—orn—orn—orn—cys;

1    2    3    4    5    6    7
P4 = aib—cys—ser—orn—orn—ser—cys;

1    2    3    4    5    6    7
P5 = aib—asp—ala—orn—orn—orn—ser;
```

-continued

```
         1    2    3    4    5    6
P6 =  aib—asp—asp—asp—asp—asp;

1    2    3    4    5    6    7
P7 =  Abu—cys—asp—asp—asp—asp—cys;

1    2    3    4    5    6    7
P8 =  aib—cys—asp—orn—orn—asp—cys;

1    2    3    4    5    6    7
P9 =  aib—phe—asp—asp—ser—ser—orn;

1    2         4         6
P10 = aib—tyr—ala—gly—ala—tyr;
``` where aib is alpha-amino isobutyric acid and Abu is 2-amino butyric acid.

In all cases, the C-terminus is capped with an amide group. Hydrophobic amino acids used (phenylalanine, alanine, valine) are the D-isomers. Positive (ornithine), negative (aspartic) and neutral hydrophilic residues (serine) have the shortest length side chains readily available. Intra-chain cyclization is via a disulfide bond between two cysteine residues.

EXAMPLE 2

Adsorption Patterns

Collection plates (Falcon) were pretreated with Tween-20 to block protein adsorption to the plastic surfaces. The protein contents in the flow-through (FT) and retained-eluted (RE) fractions from the various sorbent "columns" prepared according to Example 1 were determined using the Bio-Rad Protein Assay (Richmond, Calif.), adapted to the 96-well plate format; absorbances were read in a max Plate Reader™ using SOFTmax™ software for curve fitting (Molecular Devices, Menlo Park, Calif.). Homologous protein was used to generate a standard curve for each protein.

Charge distributions and conformation propensity status paralogs P1–P10 are summarized in Table 1.

TABLE 1

| Paralog Sorbent | Charge Structure | Paralog Sorbent | Charge Structure |
|---|---|---|---|
| P1 | +++++ | P6 | — |
| P2 | ++OO++ | P7 | ∆----∆ |
| P3 | ∆++++∆ | P8 | ∆-++-∆ |
| P4 | ∆O++O∆ | P9 | H--OO+ |
| P5 | H+++O | P10 | HHOHH |

The free amino group of the N-terminal amino acid is used for coupling to the sorbent.

The standard buffer used for preparing the sorbent slurries and sample loading was 10 mM Tris-HCl, pH 7.5, 1 mM EDTA (TE). The standard elution buffers was 10 mM Tris-HCl, pH 7.5, 1 mM EDTA, 1000 mM NaCl (TEN-1000). In variants of TEN-1000, the NaCl concentrations (mM) is indicated by the number following TEN-.

To use the "columns" for chromatography, the storage buffer was removed from the sorbent plate by centrifugation into an empty 96-well plate, and the columns were washed with 200 μL TE three times. Centrifugation steps to drain the plates were performed on a Beckman TJ-6 centrifuge (Beckman Instruments, Fullerton, Calif.), equipped with 96-well test plate carriers, at 750×g (~2000 rpm) for 2 minutes. The columns were then equilibrated in TE by the addition of 200 μL TE and incubation for 15 minutes, followed by centrifugation.

For binding profile experiments, 50 μL of a purified protein solution (1 mg/mL in TE buffer) were loaded onto each column in the sorbent plate. The plate was incubated at room temperature for 15 minutes to allow adsorption of the sample to the chromatographic sorbents, after which 50 μL of TE was added to each well and the buffer and unbound sample collected by centrifugation into the same collection plate. This microplate then contained ~150 μL of unbound or flow-through (FT) protein fraction.

For elution of any adsorbed protein, 75 μL TEN-1000 were added to each column and equilibrated for 15 minutes at room temperature. The eluted proteins were collected into a second pretreated microplate by centrifugation; followed by a second 75 μL TEN-1000 equilibration and elution step, collecting into the same plate. These samples are designated the TEN-1000 retained-eluted (RE) fraction.

For re-use, the plates were washed with 6M urea and re-equilibrated in TE prior to loading the next protein samples.

Figure 1B:
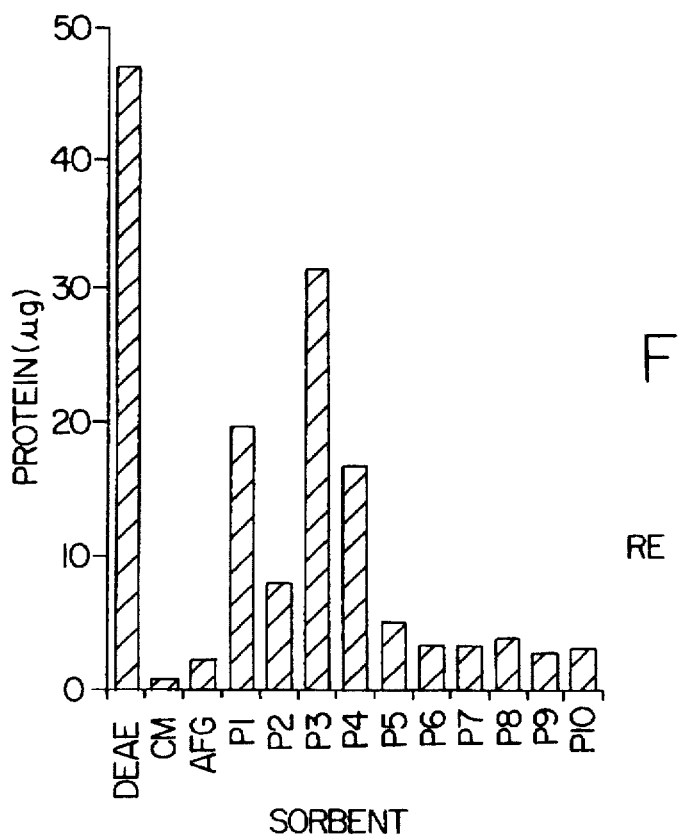

The characteristic binding profile of BSA to the paralog sorbents is shown in FIG. 1. Binding profiles were determined using DEAE, CMC, and ethanolamine-blocked Affi-Gel (AFG) as controls. The amounts of BSA in the FT and the RE fractions for each sorbent are shown in FIGS. 1A and 1B, respectively. As shown, DEAE-cellulose and paralog sorbents P1, P3, and P4 bind a significant amount of BSA, while CMC control, AFG and the remaining paralogs do not. For P1, P3 and P4, variation in affinity is shown.

Plate-to-plate reproducibility is shown in Table 2. Fifty μg BSA were loaded into each well and eluted according to the standard protocol. Using 3 different sorbent plates, the amount of protein in the FT and the RE fractions was calculated. The average coefficient of variation (standard deviation/mean) for the FT and RE fractions with significant protein content was ~15%. The mass balance averaged to 88% of starting material for all sorbents. The results are shown in Table 2.

TABLE 2

| | Flow Through | | | Retained-Eluted | | | Total Protein | | |
|---|---|---|---|---|---|---|---|---|---|
| SORBENT | Avg | Std. Dev. | % | Avg | Std. Dev. | % | Avg | Std. Dev. | % |
| DEAE | 0.0 | 0.0 | 0 | 47.3 | 4.4 | 95 | 47.3 | 4.4 | 95 |
| CM | 42.2 | 9.2 | 84 | 0.8 | 0.9 | 2 | 43.0 | 8.5 | 86 |
| AFG | 45.6 | 2.8 | 91 | 2.2 | 1.9 | 4 | 47.8 | 4.7 | 96 |
| P1 | 26.7 | 2.6 | 53 | 19.7 | 1.6 | 39 | 46.4 | 3.8 | 93 |
| P2 | 41.8 | 2.5 | 84 | 8.0 | 0.8 | 16 | 49.7 | 1.7 | 99 |
| P3 | 0.0 | 0.0 | 0 | 31.7 | 1.7 | 63 | 31.7 | 1.7 | 63 |
| P4 | 11.9 | 6.5 | 24 | 16.8 | 3.5 | 34 | 28.7 | 8.3 | 57 |
| P5 | 42.3 | 2.6 | 85 | 5.0 | 1.3 | 10 | 47.3 | 2.6 | 95 |
| P6 | 45.2 | 1.5 | 90 | 3.5 | 1.8 | 7 | 48.7 | 1.6 | 97 |
| P7 | 43.3 | 3.5 | 87 | 3.5 | 3.0 | 7 | 46.8 | 6.4 | 94 |
| P8 | 42.3 | 3.2 | 85 | 4.1 | 3.2 | 8 | 46.4 | 6.3 | 93 |
| P9 | 45.2 | 3.3 | 90 | 3.0 | 1.3 | 6 | 48.2 | 4.5 | 96 |
| P10 | 43.8 | 8.0 | 88 | 3.1 | 0.7 | 6 | 46.9 | 7.3 | 94 |

EXAMPLE 3

Stability and Regeneration

Figure 2:
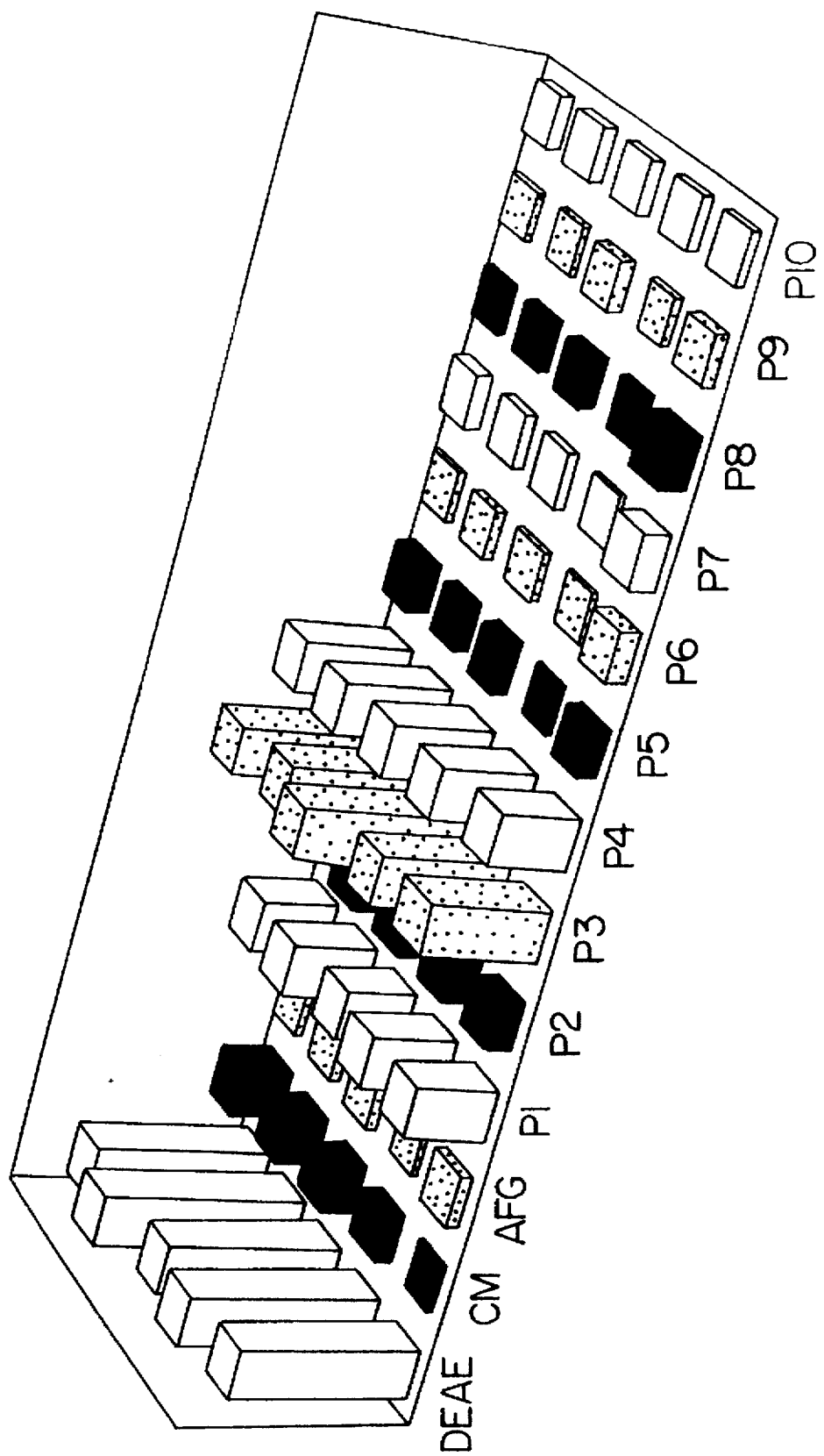
FIG. 2 shows the quantity of BSA in the retained and eluted (RE) fractions from the materials of FIG. 1 over a series of five cycles of regeneration of the sorbent.

The sorbents of the invention are also stable to denaturants, thus permitting regeneration of the sorbents by stripping all bound proteins with a strong denaturant. The columns in Example 2 were treated with 6M urea, reequilibrated in TE, and tested again for their ability to bind BSA. A total of 5 binding/elution/regeneration cycles were performed on three different sorbent plates. The results from one plate are diagrammed in FIG. 2 in a three-dimensional bar chart which displays the BSA binding profile on a panel of sorbents across 5 successive cycles.

EXAMPLE 4

Protease Resistance of the Paralog Sorbents

The paralog sorbents of the invention have both N and C termini blocked; they also incorporate several non-standard amino acids. To test the efficacy of these features in hindering proteolysis, the BSA binding capacity of fresh paralog sorbents was compared to that of sorbents incubated with 1 mg/mL trypsin solution for 30 minutes. The activity of the trypsin solution was confirmed in parallel experiments by observing release into solution of dye from azocoll, an insoluble dye-protein conjugate. After removing the trypsin, washing the sorbents with 6M urea and reequilibrating the sorbent plate in TE buffer, we repeated the BSA binding experiment. The amount of BSA bound was compatible to that shown in Table 2 indicating that at least those paralog sorbents which bind BSA are resistant to proteolysis. During a different set of experiments, we saw that trypsin treatment of plates used many times with a variety of proteins helped to restore the BSA binding characteristics, presumably by degrading irreversibly bound protein.

EXAMPLE 5

Binding Profiles of a Panel of Single Proteins

Figure 3:
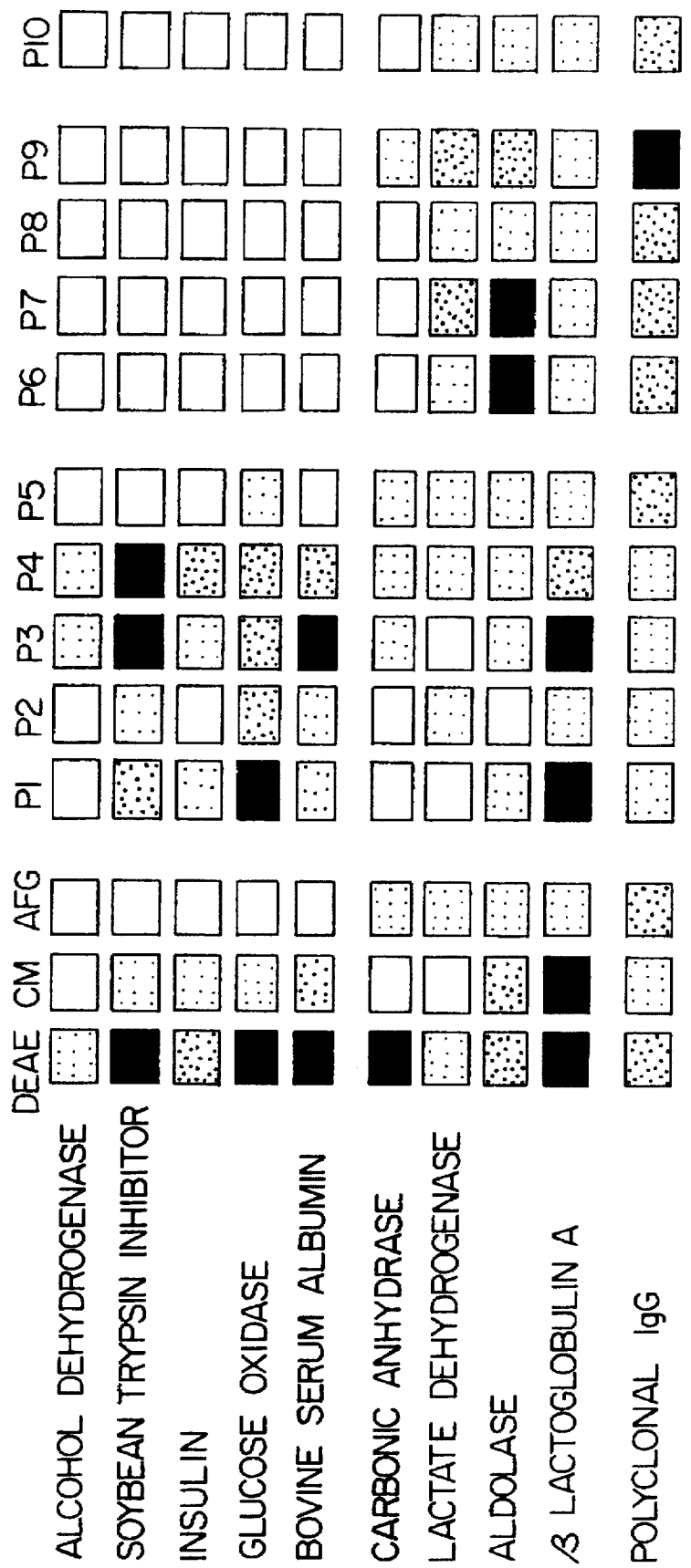
FIG. 3 shows the pattern of recovery of various proteins in retained and eluted fragments from the sorbents described in the results of FIG. 1.

After establishing the reproducibility of operations with BSA, we used the standard protocol to determine the binding profile of several other commercially available purified single proteins. The binding experiments were performed at least three times for each protein. Periodically, BSA was run on the plates as a quality assurance marker. The BSA profiles were similar to Table 2 providing additional evidence for reusability of the plates. FIG. 3 displays the binding is profile of several proteins on DEAE-cellulose, CM-cellulose, blocked Affi-Gel (AFG), and the paralog sorbents. For this figure, the results are presented as a transformed bar chart in which the height of the bars have been transferred into gray scale values. We established five levels on the gray scale, which correspond to <5, 5–15, 15–25, 25–35 and >35 μg adsorbed protein out of the 50 μg applied. FIG. 3 thus allows data for all three parameters to be easily visualized: 13 sorbents×10 proteins×5 qualitative adsorption values.

EXAMPLE 6

Measurement of the Affinity Binding Constant (Ka)
Affinity Binding Constant (Ka) Measurement Equal volumes (200 μL) of a BSA solution series at varying concentrations (2.5, 5.0, 10.0, 20.0, 50.0 mg/mL) were loaded onto 80 μL SBV "columns" of DEAE and 200 μL SBV "columns" of paralog sorbents P3 and P4 at a ligand density of ~14 μmole/mL SBV. After incubation for 15 min, the sorbents were washed with TE buffer to remove the non-adsorbed BSA. The adsorbed BSA was then eluted with TEN-1000 buffer and the protein concentration of the fraction determined. Adsorption isotherms were constructed and affinity binding constants calculated by Scatchard analysis.

Figure 4A:
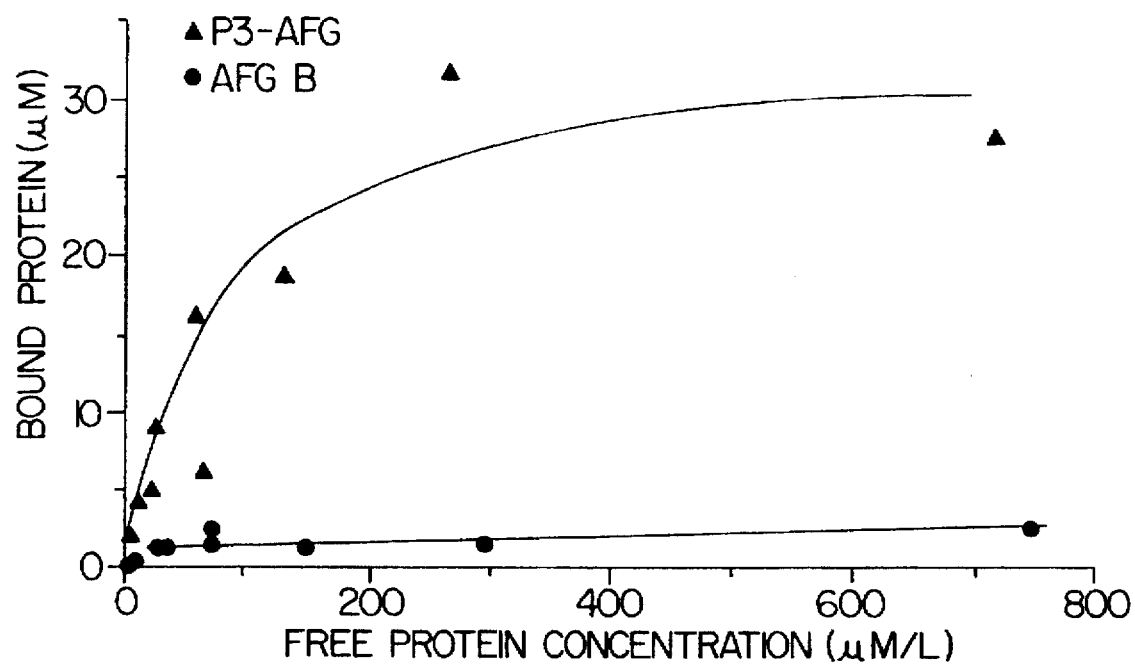
FIG. 4A shows typical data for BSA with respect to the sorbent P3 and with respect to unconjugated Affi-Gel.
Figure 4B:
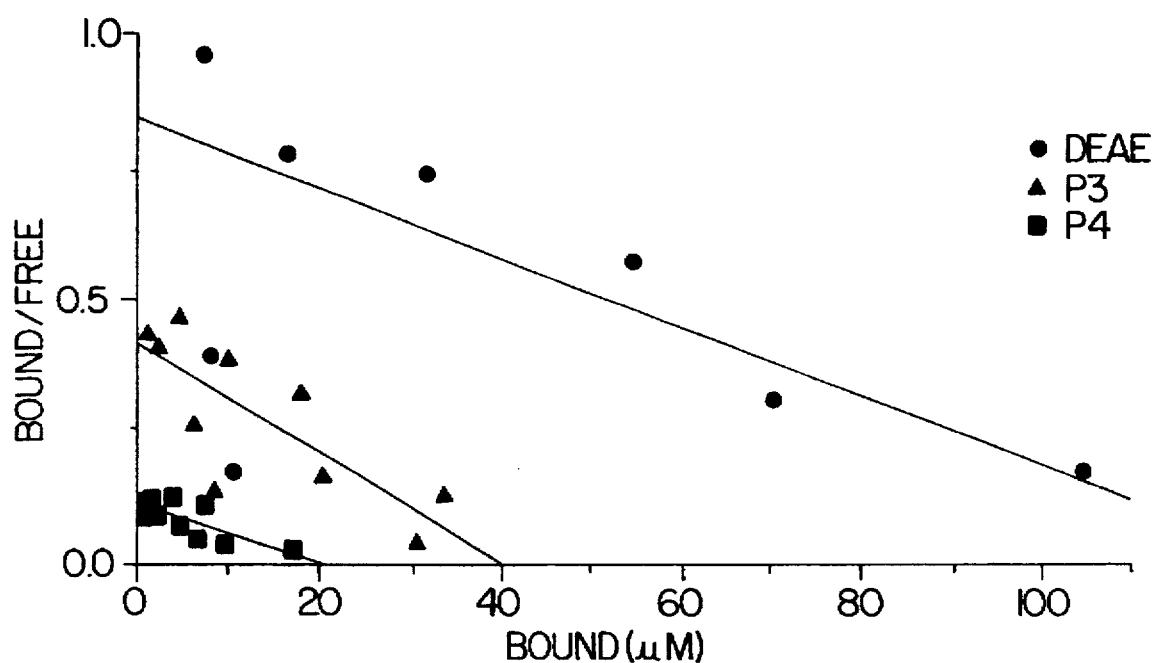
FIG. 4B shows the Scatchard analysis of the data of FIG. 4A with respect to sorbent P3 as well as data similarly obtained for sorbent P4 and for DEAE.

The results (FIG. 4) indicate that the sorbents provide binding strengths comparable to traditional ion-exchange resins,, $\sim 10^4 M^{-1}$, a range that also characterizes low to moderate affinity antibodies [14]. The affinity of protein-paralog interactions is thus in the range which is typically used for chromatographic resolution of similar proteins by repeated differential partitioning, a process not generally possible in the on/off step elution mode of traditional affinity chromatography using high:affinity ligands.

At a ligand density of 14 μmoles/ml of paralog sorbent, the capacity of P3 for BSA is about 13% the capacity of a comparable amount of DEAE-cellulose, in reasonable accord with the fact that the number of positive charges is about 9% that of DEAE-cellulose. Independently prepared batches of paralog sorbents, with constant amount of paralog put into the coupling reaction, yielded sorbents with equal ligand densities to within the accuracy of the determination. For these experiments, the amount of ligand conjugated to the solid support was estimated from the difference between ligand added to the conjugation reaction and ligand-recovered free in solution following the reaction. As a functional test, two independently prepared batches of P4 were used to generate BSA binding profiles, with the results matching to within the precision of the determination. A second pair of sorbents using paralog P4 was also prepared with half the amount of ligand attached to the solid phase; the maximal binding for BSA to these sorbents was reduced approximately by half compared to the higher ligand density sorbent.

EXAMPLE 7

Application of Paralog Sorbents to Sequential Fractionation of a Complex Protein Mixture Yeast extract, a whole cell acetone lysate, was dissolved in TE (180 mg solid in 2 mL buffer) with 10 μL of freshly prepared 50 mM PMSF added as a protease inhibitor. After centrifugation at 10,000×g for 10 minutes, the sample solution was loaded on a 5 ml SBV DEAE-cellulose column and washed with 80 mL loading buffer. The adsorbed proteins were eluted with approximately 100 mL TEN-200 buffer, dialyzed against distilled water and lyophilized. This protein mixture was then used as starting material for further fractionation experiments comparing the performance of DEAE-cellulose and selected paralog sorbents, again using the microplate format for sequential step gradient elutions. For these experiments, all fractions were collected, dialyzed, lyophilized and then analyzed by SDS-PAGE (10%) electrophoresis using silver staining as the visualization technique.

Differential binding profiles of proteins is expected to aid in protein purification. To further examine the utility of the novel sorbents in a model protein fractionation system, a complex mixture of yeast proteins was first fractionated on DEAE-cellulose using a steep NaCl gradient. The protein fractions were eluted with 0, 20, 50, 80, 100 and 140 mM NaCl in TE buffer. The 80 mM NaCl fraction was then dialyzed against TE. Following a commonly practiced protein purification strategy, that fraction was then re-fractionated on DEAE using a shallower NaCl gradient (10, 20, 30, 40, 50, 60, 70, 80, 90 and 100 mM NaCl) to provide higher resolution. In parallel, other aliquots of the same fraction were chromatographed on paralog sorbents P3 and P4, anion-exchange variants. The use of a flow-through microplate, following the protocol described above for single protein profile determinations, helped to insure that these parallel processing steps were conducted under identical conditions. Three wells of each sorbent were used, and fractions pooled, to provide enough capacity for the sequential fractionation experiments.

The SDS-PAGE analysis of the resulting fractions are provided in FIG. 5. A constant proportion of each fraction was loaded onto the gel, thus resulting in certain lanes being overloaded with regard to optimal staining for visualization of individual bands but allowing clear visualization of the differences in overall binding between the various fractions. The differences in selectivity between DEAE and the paralog sorbents are clearly illustrated in FIG. 5B. The ionic strength necessary for the elution of the protein mixtures is lower on the paralog sorbents than on DEAE-cellulose. The composition differences of the corresponding fractions (e.g., same ionic strength) collected from P3 and P4 are also distinct.

To further compare the utility of the differing selectivities provided by the family of paralog sorbents, we selected the 50 mM NaCl fraction from the secondary separation on P3 and, following dialysis against TE, subjected it to a tertiary fractionation on. sorbent P4. Similarly, the 50 mM NaCl fraction from P4 was applied to P3. The proteins in these tertiary fractionation steps on both paralog sorbents were eluted with a salt gradient containing 30, 40, 50, and 80 mM NaCl steps. The SDS-PAGE analysis of these fractions are displayed in FIG. 5C. It is evident that the composition of the analogous fractions are significantly different. These observations indicate that consecutive purification steps on different paralog sorbents can provide favorable selectivity for a variety of proteins.

I claim:

1. A compound in purified and isolated form substantially free of contamination with, or coupling to, additional substances, which compound is selected from C-terminal amidated peptides of the formula:

$$2Abu\text{-}AA_2\text{-}AA_3\text{-}AA_4\text{-}AA_5\text{-}AA_6\text{-}AA_7,$$

wherein $AA_2$ is cys, orn, lys, asp, glu, ser, gly, ala, phe or tyr;

each of $AA_3$, $AA_4$, $AA_5$ and $AA_6$ is independently orn, lys, asp, glu, ser, gly, ala, phe or tyr, $AA_7$ is absent or is cys, orn, lys, asp, glu, ser, gly, ala, phe or tyr; and wherein said peptide optionally contains one or more pseudopeptide linkages.

2. The compound of claim 1 coupled covalently or noncovalently to solid support, with the proviso that said support is not an agarose support with uncapped carboxyl groups.

3. The compound of claim 1 which is further coupled to a radiolabel, fluorescent label, or enzyme label.

4. The compound of claim 1 which is further coupled to a non-peptide linker moiety.

5. A method to separate components of a mixture chromatographically, which method comprises applying said mixture to a column comprised of the compound of claim 1 coupled to solid support, with the proviso that said support is not an agarose support with uncapped carboxyl groups, under conditions wherein some but not all of the components are adsorbed to the solid support, washing the solid support, and eluting the adsorbed components of the mixture from the solid support.

6. A method to elute a component adsorbed to a chromatographic support, which method comprises contacting said component adsorbed to chromatographic support with a solution of the compound of claim 1 under conditions wherein said compound of claim 1 effects the elution of said adsorbed component.

7. The compound of claim 1 which is selected from the group consisting of:

Abu-cys-orn-orn-orn-orn-cys-$NH_2$ (SEQ ID NO:34) and,

Abu-cys-asp-asp-asp-asp-cys-$NH_2$ (SEQ ID NO:38).

8. A compound in purified and isolated form substantially free of contamination with, or coupling to, additional substances, which compound is selected from C-terminal amidated peptides of the formula $$Aib\text{-}AA_2\text{-}AA_3\text{-}AA_4\text{-}AA_5\text{-}AA_6\text{-}AA_7,$$

wherein $AA_2$ is cys, orn, lys, asp, glu, ser, gly, ala, phe or tyr;

$AA_3$ is lys, gly, ser, gly, ala, phe or tyr;

$AA_4$ and $AA_5$ is each independently orn, lys, asp, glu, ser, gly, ala, phe or tyr;

$AA_6$ is lys, glu, gly, ala, phe or tyr; and $AA_7$ is absent or is cys, orn, lys, asp, glu, ser, gly, ala, phe or tyr; and wherein said peptide optionally contains one or more pseudopeptide linkages.

9. The compound of claim 8 coupled covalently or noncovalently to solid support, with the proviso that said support is not an agarose support with uncapped carboxyl groups.

10. The compound of claim 8 which is further coupled to a radiolabel, fluorescent label, or enzyme label.

11. The compound of claim 8 which is further coupled to a non-peptide linker moiety.

12. A method to separate components of a mixture of biological substances chromatographically, which method comprises applying said mixture to a column comprised of the compound of claim 8 coupled to solid support, with the proviso that said support is not an agarose support with uncapped carboxyl groups, under conditions wherein some but not all of the components are adsorbed to the solid support, washing the solid support, and eluting the adsorbed components of the mixture from the solid support.

13. A method to elute a biological substance adsorbed to a chromatographic support, which method comprises contacting said biological substance adsorbed to chromatographic support with a solution of the compound of claim 8 under conditions wherein said compound of claim 8 effects the elution of said adsorbed biological substance.

14. A compound in purified and isolated form substantially free of contamination with, or coupling to, additional substances which compound is selected from Aib-orn-orn-orn-orn-orn-NH$_2$ (SEQ ID NO:32),
Aib-orn-orn-ser-ser-orn-orn-NH$_2$ (SEQ ID NO:33),
Aib-cys-ser-orn-orn-ser-cys-NH$_2$ (SEQ ID NO:35),
Aib-asp-ala-orn-orn-orn-ser-NH$_2$ (SEQ ID NO:36),
Aib-cys-asp-orn-orn-asp-cys-NH$_2$ (SEQ ID NO:39), and
Aib-tyr-D-ala-gly-D-ala-tyr-NH$_2$ (SEQ ID NO:41)

wherein said peptide optionally contains one or more pseudopeptide linkages.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "X represents either the
        amino acid alpha-amino isobutyric acid(Aib) or
        2- aminobutyric acid(2ab)"

( i x ) FEATURE:
        ( A ) NAME/KEY: Modified-site
        ( B ) LOCATION: 2
        ( D ) OTHER INFORMATION: /note= "X represents the amino acid
        cysteine(cys), ornithine(orn), lysine(lys),
        asparagine(asp), glutamic acid(glu), serine(ser),
        glycine(gly), alanine(ala), phenylalanine(phe) or
        tyrosine(tyr)."

( i x ) FEATURE:
        ( A ) NAME/KEY: Modified-site
        ( B ) LOCATION: 3..6
        ( D ) OTHER INFORMATION: /note= "Each X represents
        independently orn, lys, asp, glu, ser, gly, ala, phe
        or tyr."

( i x ) FEATURE:
        ( A ) NAME/KEY: Modified-site
        ( B ) LOCATION: 7
        ( D ) OTHER INFORMATION: /note= "X represents an amino acid
        that is absent or is cys, orn, lys, asp, glu, ser, gly,
        ala, phe or tyr."

( x i ) SEQUENCE DESCRIPTION: SEQ ID NO:1:

Xaa Xaa Xaa Xaa Xaa Xaa Xaa
    1                     5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: group(3, 4, 5, 6)
    ( D ) OTHER INFORMATION: /product="Orn"

( i x ) FEATURE:
    ( A ) NAME/KEY: Modified-site
    ( B ) LOCATION: 1
    ( D ) OTHER INFORMATION: /product="Aib"

( i x ) FEATURE:
    ( A ) NAME/KEY: Modified-site
    ( B ) LOCATION: 6
    ( D ) OTHER INFORMATION: /label= - NH2
            / note= "C-terminus amidated"

( x i ) SEQUENCE DESCRIPTION: SEQ ID NO:2:

Xaa Lys Xaa Xaa Xaa Xaa
1                5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(2, 6, 7)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
                / note= "C-terminus amidated"

( x i ) SEQUENCE DESCRIPTION: SEQ ID NO:3:

Xaa Xaa Lys Ser Ser Xaa Xaa
1                5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site
        ( B ) LOCATION: group(4, 6)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
                / note= "C-terminus is amidated"

( x i ) SEQUENCE DESCRIPTION: SEQ ID NO:4:

Xaa Cys Lys Xaa Lys Xaa Cys ( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 4
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:5:

Xaa  Cys  Ser  Xaa  Lys  Ser  Cys
    1                      5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(2, 4, 5, 6)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:6:

Xaa  Xaa  Ala  Xaa  Xaa  Xaa  Ser
    1                      5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 6
        ( D ) OTHER INFORMATION: /product="Orn"

-continued

```
( i x ) FEATURE:
        ( A ) NAME/KEY: Modified-site
        ( B ) LOCATION: 6
        ( D ) OTHER INFORMATION: /label= - NH2
                / note= "C-terminus is amidated"

( x i ) SEQUENCE DESCRIPTION: SEQ ID NO:7:

Xaa   Lys   Lys   Lys   Lys   Xaa
1                       5
```

( 2 ) INFORMATION FOR SEQ ID NO:8:

```
( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site
        ( B ) LOCATION: group(3, 5, 6)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
                / note= "C-terminus is amidated"

( x i ) SEQUENCE DESCRIPTION: SEQ ID NO:8:

Xaa   Cys   Xaa   Ala   Xaa   Xaa   Cys
1                       5
```

( 2 ) INFORMATION FOR SEQ ID NO:9:

```
( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(4, 5)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
                / note= "C-terminus is amidated"

( x i ) SEQUENCE DESCRIPTION: SEQ ID NO:9:

Xaa   Cys   Asp   Xaa   Xaa   Lys   Cys
1                       5
```

( 2 ) INFORMATION FOR SEQ ID NO:10:

```
( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear
```

( i x ) FEATURE:
    ( A ) NAME/KEY: Modified-site
    ( B ) LOCATION: 1
    ( D ) OTHER INFORMATION: /product="Aib"

( i x ) FEATURE:
    ( A ) NAME/KEY: Modified-site
    ( B ) LOCATION: group(3, 4, 5, 8)
    ( D ) OTHER INFORMATION: /product="Orn"

( i x ) FEATURE:
    ( A ) NAME/KEY: Modified-site
    ( B ) LOCATION: 8
    ( D ) OTHER INFORMATION: /label= - NH2
        / note= "C-terminus is amidated"

( x i ) SEQUENCE DESCRIPTION: SEQ ID NO:10:

Xaa Phe Xaa Xaa Xaa Ser Ser Xaa
1               5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 4
        ( D ) OTHER INFORMATION: /product="Orn"

( i x ) FEATURE:
        ( A ) NAME/KEY: Modified-site
        ( B ) LOCATION: 6
        ( D ) OTHER INFORMATION: /label= - NH2
            / note= "C-terminus is amidated"

( x i ) SEQUENCE DESCRIPTION: SEQ ID NO:11:

Xaa Tyr Ala Xaa Ala Tyr
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 6
        ( D ) OTHER INFORMATION: /label= - NH2
            / note= "C-terminus is amidated"

( x i ) SEQUENCE DESCRIPTION: SEQ ID NO:12:

Xaa Asp Glu Asp Asp Glu
1               5

( 2 ) INFORMATION FOR SEQ ID NO:13:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /product="Aib"

( i x ) FEATURE:
    ( A ) NAME/KEY: Modified-site
    ( B ) LOCATION: 7
    ( D ) OTHER INFORMATION: /label= - NH2
        / note= "C-terminus is amidated"

( x i ) SEQUENCE DESCRIPTION: SEQ ID NO:13:

Xaa Asp Glu Ser Ser Asp Asp
1                 5

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:14:

Xaa Cys Glu Gly Glu Gly Cys
1                 5

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 7
        ( D ) OTHER INFORMATION: /label= - NH2
            / note= "C-terminus amidated"

( x i ) SEQUENCE DESCRIPTION: SEQ ID NO:15:

Xaa Cys Ser Asp Glu Ser Cys
1                 5

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 1
    ( D ) OTHER INFORMATION: /product="Aib"

( i x ) FEATURE:
    ( A ) NAME/KEY: Modified-site
    ( B ) LOCATION: 6
    ( D ) OTHER INFORMATION: /product="Orn"

( i x ) FEATURE:
    ( A ) NAME/KEY: Modified-site
    ( B ) LOCATION: 7
    ( D ) OTHER INFORMATION: /label= - NH2
       / note= "C-terminus is amidated"

( x i ) SEQUENCE DESCRIPTION: SEQ ID NO:16:

Xaa Asp Ala Glu Glu Xaa Ser
1               5

( 2 ) INFORMATION FOR SEQ ID NO:17:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /product="Abu"

( i x ) FEATURE:
    ( A ) NAME/KEY: Modified-site
    ( B ) LOCATION: 6
    ( D ) OTHER INFORMATION: /label= - NH2
       / note= "C-terminus is amidated"

( x i ) SEQUENCE DESCRIPTION: SEQ ID NO:17:

Xaa Asp Asp Asp Asp Asp
1            5

( 2 ) INFORMATION FOR SEQ ID NO:18:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /product="Abu"

( i x ) FEATURE:
    ( A ) NAME/KEY: Modified-site
    ( B ) LOCATION: 7
    ( D ) OTHER INFORMATION: /label= - NH2
       / note= "C-terminus is amidated"

( x i ) SEQUENCE DESCRIPTION: SEQ ID NO:18:

Xaa Cys Glu Asp Ser Asp Cys
1               5

( 2 ) INFORMATION FOR SEQ ID NO:19:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
 ( A ) NAME/KEY: Modified-site
 ( B ) LOCATION: 1
 ( D ) OTHER INFORMATION: /product="Aib"

( i x ) FEATURE:
 ( A ) NAME/KEY: Modified-site
 ( B ) LOCATION: 4
 ( D ) OTHER INFORMATION: /product="Orn"

( i x ) FEATURE:
 ( A ) NAME/KEY: Modified-site
 ( B ) LOCATION: 7
 ( D ) OTHER INFORMATION: /label= - NH2
  / note= "C-terminus is amidated"

( x i ) SEQUENCE DESCRIPTION: SEQ ID NO:19:

Xaa Cys Asp Xaa Glu Asp Cys
1               5

( 2 ) INFORMATION FOR SEQ ID NO:20:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i x ) FEATURE:
 ( A ) NAME/KEY: Modified-site
 ( B ) LOCATION: 1
 ( D ) OTHER INFORMATION: /product="Abu"

( i x ) FEATURE:
 ( A ) NAME/KEY: Modified-site
 ( B ) LOCATION: 8
 ( D ) OTHER INFORMATION: /product="Orn"

( i x ) FEATURE:
 ( A ) NAME/KEY: Modified-site
 ( B ) LOCATION: 8
 ( D ) OTHER INFORMATION: /label= - NH2
  / note= "C-terminus is amidated"

( x i ) SEQUENCE DESCRIPTION: SEQ ID NO:20:

Xaa Phe Asp Glu Asp Ser Ser Xaa
1               5

( 2 ) INFORMATION FOR SEQ ID NO:21:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i x ) FEATURE:
 ( A ) NAME/KEY: Modified-site
 ( B ) LOCATION: 1
 ( D ) OTHER INFORMATION: /product="Aib"

( i x ) FEATURE:
 ( A ) NAME/KEY: Modified-site
 ( B ) LOCATION: 6
 ( D ) OTHER INFORMATION: /label= - NH2
  / note= "C-terminus is amidated"

( x i ) SEQUENCE DESCRIPTION: SEQ ID NO:21:

Xaa Tyr Asp Gly Ala Tyr
1               5

( 2 ) INFORMATION FOR SEQ ID NO:22:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /product="Aib"

( i x ) FEATURE:
    ( A ) NAME/KEY: Modified-site
    ( B ) LOCATION: 6
    ( D ) OTHER INFORMATION: /label= - NH2
        / note= "C-terminus is amidated"

( x i ) SEQUENCE DESCRIPTION: SEQ ID NO:22:

Xaa Gly Ser Ser Gly Ser
1               5

( 2 ) INFORMATION FOR SEQ ID NO:23:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(2, 6, 7)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:23:

Xaa Xaa Asp Ser Ser Xaa Xaa
1               5

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site
        ( B ) LOCATION: group(3, 6)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:24:

Xaa Cys Xaa Glu Glu Xaa Cys ( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 4
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:25:

Xaa Cys Ser Xaa Asp Ser Cys
1                 5

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 6
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:26:

Xaa Asp Ala Glu Ala Xaa Ser
1                 5

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 6
        ( D ) OTHER INFORMATION: /label= - NH2

/ note= "C-terminus is amidated"

( x i ) SEQUENCE DESCRIPTION: SEQ ID NO:27:

Xaa Lys Asp Lys Asp Ser
1                   5

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site
        ( B ) LOCATION: 5
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:28:

Xaa Cys Lys Asp Xaa Asp Cys
1                   5

( 2 ) INFORMATION FOR SEQ ID NO:29:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 5
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:29:

Xaa Cys Ala Ala Xaa Asp Cys
1                   5

( 2 ) INFORMATION FOR SEQ ID NO:30:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
    ( A ) NAME/KEY: Modified-site
    ( B ) LOCATION: 8
    ( D ) OTHER INFORMATION: /product="Orn"

( i x ) FEATURE:
    ( A ) NAME/KEY: Modified-site
    ( B ) LOCATION: 8
    ( D ) OTHER INFORMATION: /label= - NH2
        / note= "C-terminus is amidated"

( x i ) SEQUENCE DESCRIPTION: SEQ ID NO:30:

```
Xaa Phe Ala Asp Ala Ser Ser Xaa
 1                   5
```

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 6
        ( D ) OTHER INFORMATION: /label= - NH2
            / note= "C-terminus is amidated"

( x i ) SEQUENCE DESCRIPTION: SEQ ID NO:31:

```
Xaa Phe Ala Ser Ala Tyr
 1                   5
```

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(2, 3, 4, 5, 6)
        ( D ) OTHER INFORMATION: /product="Orn"

( i x ) FEATURE:
        ( A ) NAME/KEY: Modified-site
        ( B ) LOCATION: 6
        ( D ) OTHER INFORMATION: /label= - NH2
            / note= "C-terminus is amidated"

( x i ) SEQUENCE DESCRIPTION: SEQ ID NO:32:

```
Xaa Xaa Xaa Xaa Xaa Xaa
 1                   5
```

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
    ( A ) NAME/KEY: Modified-site
    ( B ) LOCATION: 1
    ( D ) OTHER INFORMATION: /product="Aib"

( i x ) FEATURE:
    ( A ) NAME/KEY: Modified-site
    ( B ) LOCATION: group(2, 3, 6, 7)
    ( D ) OTHER INFORMATION: /product="Orn"

( i x ) FEATURE:
    ( A ) NAME/KEY: Modified-site
    ( B ) LOCATION: 7
    ( D ) OTHER INFORMATION: /product=""
          / label= -NH2
          / note= "C-terminus is amidated"

( x i ) SEQUENCE DESCRIPTION: SEQ ID NO:33:

Xaa Xaa Xaa Ser Ser Xaa Xaa
1               5

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site
        ( B ) LOCATION: group(3, 4, 5, 6)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
              / note= "C-terminus is amidated"

( x i ) SEQUENCE DESCRIPTION: SEQ ID NO:34:

Xaa Cys Xaa Xaa Xaa Xaa Cys
1               5

( 2 ) INFORMATION FOR SEQ ID NO:35:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(4, 5)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
              / note= "C-terminus is amidated"

( x i ) SEQUENCE DESCRIPTION: SEQ ID NO:35:

```
Xaa Cys Ser Xaa Xaa Ser Cys
 1               5
```

( 2 ) INFORMATION FOR SEQ ID NO:36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 2
        ( D ) OTHER INFORMATION: /product="OTHER"
            / note= "D-alanine"

( i x ) FEATURE:
        ( A ) NAME/KEY: Modified-site
        ( B ) LOCATION: group(4, 5, 6)
        ( D ) OTHER INFORMATION: /product="Orn"

( i x ) FEATURE:
        ( A ) NAME/KEY: Modified-site
        ( B ) LOCATION: 7
        ( D ) OTHER INFORMATION: /label= - NH2
            / note= "C-terminus is amidated"

( x i ) SEQUENCE DESCRIPTION: SEQ ID NO:36:

```
Xaa Asp Xaa Xaa Xaa Xaa Ser
 1               5
```

( 2 ) INFORMATION FOR SEQ ID NO:37:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: 6
        ( D ) OTHER INFORMATION: /label= - NH2
            / note= "C-terminus is amidated"

( x i ) SEQUENCE DESCRIPTION: SEQ ID NO:37:

```
Xaa Asp Asp Asp Asp Asp
 1               5
```

( 2 ) INFORMATION FOR SEQ ID NO:38:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Abu"

( i x ) FEATURE:
        ( A ) NAME/KEY: Modified-site (B) LOCATION: 7
(D) OTHER INFORMATION: /label=- NH2
/ note= "C-terminus is amidated"

(xi) SEQUENCE DESCRIPTION: SEQ ID NO:38:

Xaa Cys Asp Asp Asp Asp Cys
1               5

(2) INFORMATION FOR SEQ ID NO:39:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /product="Aib"

(ix) FEATURE:
    (A) NAME/KEY: Modified-site
    (B) LOCATION: group(4, 5)
    (D) OTHER INFORMATION: /product="Orn"

(ix) FEATURE:
    (A) NAME/KEY: Modified-site
    (B) LOCATION: 7
    (D) OTHER INFORMATION: /label=- NH2
    / note= "C-terminus is amidated"

(xi) SEQUENCE DESCRIPTION: SEQ ID NO:39:

Xaa Cys Asp Xaa Xaa Asp Cys
1               5

(2) INFORMATION FOR SEQ ID NO:40:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /product="Aib"

(ix) FEATURE:
    (A) NAME/KEY: Modified-site
    (B) LOCATION: 2
    (D) OTHER INFORMATION: /product="OTHER"
    / note= "D-phenylalanine"

(ix) FEATURE:
    (A) NAME/KEY: Modified-site
    (B) LOCATION: 7
    (D) OTHER INFORMATION: /product="Orn"

(ix) FEATURE:
    (A) NAME/KEY: Modified-site
    (B) LOCATION: 7
    (D) OTHER INFORMATION: /label=- NH2
    / note= "C-terminus is amidated"

(xi) SEQUENCE DESCRIPTION: SEQ ID NO:40:

Xaa Xaa Asp Asp Ser Ser Xaa
1               5

(2) INFORMATION FOR SEQ ID NO:41:

(i) SEQUENCE CHARACTERISTICS:
    (A) LENGTH: 6 amino acids

```
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="Aib"

( i x ) FEATURE:
        ( A ) NAME/KEY: Modified-site
        ( B ) LOCATION: group(3, 5)
        ( D ) OTHER INFORMATION: /product="OTHER"
                / note= "D-alanine"

( i x ) FEATURE:
        ( A ) NAME/KEY: Modified-site
        ( B ) LOCATION: 6
        ( D ) OTHER INFORMATION: /label= - NH2
                / note= "C-terminus is amidated"

( x i ) SEQUENCE DESCRIPTION: SEQ ID NO:41:

Xaa  Tyr  Xaa  Gly  Xaa  Tyr
    1                 5
```